(12) United States Patent
Jolivet et al.

(10) Patent No.: US 6,645,972 B2
(45) Date of Patent: Nov. 11, 2003

(54) METHODS OF TREATING LEUKEMIA

(75) Inventors: Jacques Jolivet, Laval (CA); Francis Giles, Houston, TX (US); Hagop Kantarjian, Houston, TX (US)

(73) Assignee: Shire BioChem Inc., Quebec (CA)

( * ) Notice: Subject to any disclaimer, the term of this patent is extended or adjusted under 35 U.S.C. 154(b) by 0 days.

(21) Appl. No.: 10/286,960

(22) Filed: Nov. 4, 2002

(65) Prior Publication Data

US 2003/0125305 A1 Jul. 3, 2003

Related U.S. Application Data (60) Provisional application No. 60/330,891, filed on Nov. 2, 2001.

(51) Int. Cl.$^7$ ..................... A61K 31/505; A61K 31/675
(52) U.S. Cl. ................... 514/274; 514/86; 514/908; 514/922; 514/88; 514/252.18; 514/253.01
(58) Field of Search ........................... 514/274, 252.18, 514/253.01, 88, 86, 908, 922

(56) References Cited

U.S. PATENT DOCUMENTS 5,817,667 A * 10/1998 Chu et al. ................... 544/310
6,069,250 A * 5/2000 Mansour et al. ............ 544/264

FOREIGN PATENT DOCUMENTS

| WO | WO 9607413 A1 | 3/1996 |
| WO | WO 00/57861 A2 | 10/2000 |
| WO | WO 02/0024 A1 * | 1/2002 |

OTHER PUBLICATIONS

Giles F. J. et al., "Troxacitabine, a novel dioxolane nucleoside analog, has activity in patients with advanced leukemia", Journal of Clinical Onocology: Official Journal of the American Society of Clinical Onocology. United States, Feb. 1, 2001, vol. 19, No. 3, pp. 762–771, XP009007304.

"Gleevec (STI–571) for chronic myeloid leukemia", Medical Letter on Drugs and Therapeutics, New Rochelle, NY, US, Jun. 11, 2001, vol. 43, No. 1106, pp. 49–50, XP001036570.

"FDA approves Gleevec for leukemia treatment", FDA Consumer, United States, Jul.–Aug. 2001, vol. 35, No. 4, p. 6, XP002234140.

Giles F. et al., "Phase II study of troxatylTM in patients with chronic myeloid leukemia in blastic phase (CML–BP)", Blood, Nov. 16, 2001, vol. 98, No. 11 Part 2, p. 258b, XP002234141.

* cited by examiner

Primary Examiner—Frederick Krass
(74) Attorney, Agent, or Firm—Millen, White, Zelano, Branigan, P.C.

(57) ABSTRACT

The present invention provides a novel method for treating leukemia in a host that has been previously treated with a Bcr-Abl tyrosine kinase inhibitor comprising administering to the host a therapeutically effective amount of a compound having the formula I:

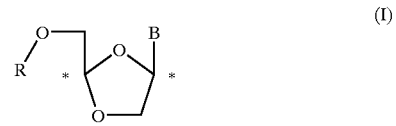

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

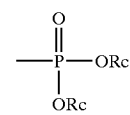

and where in each Rc is independently selected from the group comprising H, $C_{1-6}$ alkyl, $C_{2-6}$ alkenyl, $C_{2-6}$ alkynyl an hydroxy protecting group.

31 Claims, 4 Drawing Sheets

METHODS OF TREATING LEUKEMIA

This application claims the benefit of U.S. Provisional Application Ser. No. 60/330,891 filed Nov. 2, 2001 which is hereby incorporated in its entirety.

FIELD OF THE INVENTION

The present invention relates to methods for treating leukemia, and more particularly, to the use of nucleoside analogues as an effective treatment for acute or chronic myelogenous leukemia.

BACKGROUND OF THE INVENTION

Leukemia is a malignant cancer of the bone marrow and blood. It is characterized by the uncontrolled growth of blood cells. The common types of leukemia are divided into four categories: acute or chronic myelogenous, involving the myeloid elements of the bone marrow (white cells, red cells, megakaryocytes) and acute or chronic lymphocytic, involving the cells of the lymphoid lineage.

Acute leukemia is a rapidly progressing disease that results in the massive accumulation of immature, functionless cells (blasts) in the marrow and blood. The marrow often can no longer produce enough normal red and white blood cells and platelets. Anemia, a deficiency of red cells, develops in virtually all leukemia patients. The lack of normal white cells impairs the body's ability to fight infections. A shortage of platelets results in bruising and easy bleeding. In contrast, chronic leukemia progresses more slowly and leads to unregulated proliferation and hence marked overexpansion of a spectrum of mature (differentiated) cells. In general, acute leukemia, unlike the chronic form, is potentially curable by elimination of the neoplastic clone.

Treatment of leukemia is very complex and depends upon the type of leukemia. Tremendous clinical variability among remissions is also observed in leukemic patients, even those that occur after one course of therapy. Patients who are resistant to therapy have very short survival times, regardless of when the resistance occurs.

Standard treatment for leukemia usually involves chemotherapy and/or bone marrow transplantation and/or radiation therapy. The two major types of bone marrow transplants are autologus (uses the patient's own marrow) and allogeneic (uses marrow from a compatible donor). Radiation therapy, which involves the use of high-energy rays, and chemotherapy are usually given before bone marrow transplantation to kill all leukemic cells. In the cure for CML, bone marrow transplantation can be clearly curative. However, only 30% to 40% of patients with CML have an appropriate donor. Beyond that, the mortality from the procedure ranges from 20% to 30%, depending on the age of the recipient. Finally, this procedure is quite expensive.

Chemotherapy in leukemia may involve a combination of two or more anti-cancer drugs. Approximately 40 different drugs are now being used in the treatment of leukemia, either alone or in combination. Some common combinations include cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine and daunorubicin with vincristine and prednisone.

Other treatments for leukemia also include the reversal of multidrug resistance, involving the use of agents which decrease the mechanisms allowing the malignant cells to escape the damaging effects of the chemotherapeutic agent (and leads to refractoriness or relapses); and biological therapy, involving the use of substances known as biological response modifiers (BRMs). These substances are normally produced in small amounts as part of the body's natural response to cancer or other diseases. Types of BRMs include monoclonal antibodies, in which toxins are attached to antibodies that react with the complementary antigen carried by the malignant cells; and cytokines (e.g. interferons, interleukins, colony-stimulating factors CSFs) which are naturally occuring chemicals that stimulate blood cell production and help restore blood cell counts more rapidly after treatment. Examples of these drugs include multidrug resistance reversing agent PSC 833, the monoclonal antibody Rituxan and the following cytokines: Erythropoetin and Epoetin, which stimulate the production of red cells; G-CSF, GM-CSF, filgrastim, and Sargramostim which stimulate the production of white cells; and thrombopoietin, which stimulate the production of platelets.

Many nucleoside analogues have been found to possess anticancer activity. Cytarabine, Fludarabine, Gemcitabine and Cladribine are some examples of nucleoside analogues which are currently important drugs in the treatment of leukemia. β-L-OddC ((-)-β-L-Dioxolane-Cytidine, Troxatyl™, from Shire BioChem Inc.) is also a nucleoside analogue which was first described as an antiviral agent by Belleau et al. (EP 337713) and was shown to have potent antitumor activity (K. L. Grove et al., Cancer Res., 55(14), 3008–11, 1995; K. L. Grove et al., Cancer Res., 56(18), 4187–4191, 1996, K. L. Grove et al., Nucleosides Nucleotides, 16:1229–33, 1997; S. A Kadhim et al., Can. Cancer Res., 57(21), 4803–10, 1997). In clinical studies, β-L-OddC has been reported to have significant activity in patients with advanced leukemia (Giles et al., J. Clin. Oncology, Vol 19, No 3, 2001).

More recently, STI-571 (Gleevec™, imatinib mesylate, from Novartis Pharmaceuticals Corp.) a Bcr-Abl tyrosine kinase inhibitor has shown significant antileukemic activity and specifically in chronic myeologenous leukemia. STI-571 has become a promising therapy in the group of patients targeting Bcr-Abl tyrosine kinase inhibition. However, despite significant hematologic and cytogenic responses, resistance occurs particularly in the advanced phases of chronic myelogenous leukemia. Therefore, there is a great need for the further development of agents for the treatment of leukemia patients who have been previously treated with a Bcr-Abl tyrosine kinase inhibitor and have become resistant to the Bcr-Abl tyrosine kinase inhibitor.

SUMMARY OF THE INVENTION

The present invention provides a novel method for treating leukemia in a host comprising administering to a patient that has been previously treated with a Bcr-Abl tyrosine kinase inhibitor a therapeutically effective amount of a compound having the formula (1):

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and wherein each Rc is independently selected from the group comprising H, $C_{1-6}$ alkyl, $C_{2-6}$ alkenyl, $C_{2-6}$ alkynyl and an hydroxy protecting group.

In another embodiment, there is provided a method for treating leukemia in a host comprising administering to a patient that has been previously treated with with a Bcr-Abl tyrosine kinase inhibitor and who has had no previous chemotherapy treatment a therapeutically effective amount of a compound of formula (I), as defined above.

In another embodiment, there is provided a method for treating leukemia in a host comprising administering to a patient that has been previously treated with a Bcr-Abl tyrosine kinase inhibitor a therapeutically effective amount of a compound according to formula (I), as defined above.

In another embodiment, there is provided a method for treating leukemia in a host comprising administering to a patient that has been previously treated with a Bcr-Abl tyrosine kinase inhibitor and has become resistant to the Bcr-Abl tyrosine kinase inhibitor treatment, a therapeutically effective amount of a compound according to formula (I), as defined above.

In another embodiment, there is provided a method for treating leukemia in a host comprising administering to a patient that has been previously treated with a Bcr-Abl tyrosine kinase inhibitor a therapeutically effective amount of a compound according to formula (I), as defined above, and at least one further therapeutic agent selected from the group comprising nucleoside analogues; chemotherapeutic agents; multidrug resistance reversing agents; and biological response modifiers.

In another embodiment, there is provided a pharmaceutical composition for treating leukemia in a patient that has been previously treated with a Bcr-Abl tyrosine kinase inhibitor comprising at least one compound according to formula (I), as defined above, and at least one further therapeutic agent selected from the group comprising nucleoside analogues; chemotherapeutic agents; multidrug resistance reversing agents; and biological response modifiers.

Still another embodiment, there is provided a pharmaceutical composition for treating leukemia in a patient that has been previously treated with a Bcr-Abl tyrosine kinase inhibitor comprising at least one compound according to formula (I), as defined above, together with at least one pharmaceutically acceptable carrier or excipient.

In another embodiment of the invention is the use of a compound according to formula (I), as defined above, for the manufacture of a medicament for treating leukemia in a patient that has been previously treated with a Bcr-Abl tyrosine kinase inhibitor.

DETAILED DESCRIPTION OF THE INVENTION

The present invention provides a novel method for treating leukemia in a host comprising administering to a patient that has been previously treated with a Bcr-Abl tyrosine kinase inhibitor a therapeutically effective amount of a compound having the formula (I):

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and wherein each Rc is independently selected from the group comprising H, $C_{1-6}$ alkyl, $C_{2-6}$ alkenyl, $C_{2-6}$ alkynyl and an hydroxy protecting group.

In another embodiment of the invention, in the compound of formula (I), R is H.

In another embodiment, in the compound of formula (I), B is cytosine.

Alternatively, in another embodiment, in the compound of formula (I), B is 5-fluorocytosine.

In one embodiment, a compound of formula (I) is (−)-β-L-Dioxolane-Cytidine (β-L OddC).

In another embodiment, a compound of formula (I) is (−)-β-Dioxolane-5-fluoro-Cytidine (5-FddC).

In another embodiment, the compounds of formula (I) of the present invention are substantially in the form of the (−) enantiomer.

In a further embodiment, the compounds of formula (I) of the present invention are in the form of the (−) enantiomer at least 95% free of the corresponding (+) enantiomer.

In another embodiment, the compounds of formula (I) of the present invention are in the form of the (−) enantiomer at least 97% free of the corresponding (+) enantiomer.

Still in another embodiment, the compounds of formula (I) of the present invention are in the form of the (−) enantiomer at least 99% free of the corresponding (+) enantiomer.

It will be appreciated by those skilled in the art that the compounds of formula (I) contain at least two chiral centres which are marked by an asterisk (*) on formula (I). The compounds of formula (I) thus exist in the form of two different optical isomers (i.e. (+) or (−) enantiomers or β-L and β-D). All such enantiomers and mixtures thereof including racemic mixtures are included within the scope of the invention. The single optical isomer or enantiomer can be obtained by methods well known in the art, such as chiral HPLC, enzymatic resolution and the use of chiral auxiliary.

By "substantially" is meant that there is more of the (−) enantiomer than the (+) enantiomer.

In one embodiment, the present invention provides a novel method for treating leukemia in a host comprising administering to a patient that has been previously treated with a Bcr-Abl tyrosine kinase inhibitor and who has had no previous chemotherapy treatment a therapeutically effective amount of a compound having the formula (I), as defined above.

In one embodiment, the present invention provides a novel method for treating leukemia in a host comprising administering to a patient that has been previously treated with STI-571 and has become resistant to the STI-571 treatment, a therapeutically effective amount of a compound having the formula (I), as defined above.

In one embodiment, the present invention provides a novel method for treating leukemia in a host comprising administering to a patient that has been previously treated with STI-571 and has become resistant to the STI-571 treatment, a therapeutically effective amount of β-L OddC.

In another embodiment, there is provided a method for treating leukemia in a host comprising administering to a patient that has been previously treated with STI-571 a therapeutically effective amount of a compound according to formula (I), as defined above, and at least one further therapeutic agent selected from the group comprising nucleoside analogues; chemotherapeutic agents; multidrug resistance reversing agents; and biological response modifiers.

In another embodiment, the chemotherapeutic agents are selected from the group consisting of Asparaginase, Bleomycin, Busulfan, Carmustine, Chlorambucil, Cladribine, Cyclophosphamide, Cytarabine, Dacarbazine, Daunorubicin, Doxorubicin, Etoposide, Fludarabine, Gemcitabine, Hydroxyurea, Idarubicin, Ifosfamide, Lomustine, Mechlorethamine, Melphalan, Mercaptopurine, Methotrexate, Mitomycin, Mitoxantrone, Pentostatin, Procarbazine, 6-Thioguanine, Topotecan, Vinblastine, Vincristine, Dexamethasone, Retinoic acid and Prednisone.

In one embodiment, a further therapeutic agent is a nucleoside analogue.

In one embodiment, a further therapeutic agent is a cytosine nucleoside analogue.

In another embodiment, a further therapeutic agent is a cytosine nucleoside analogue chosen from Cytarabine (Ara-C) or Gemcitabine.

In another embodiment, a further therapeutic agent is Idarubicin.

In one embodiment, the multidrug resistance reversing agent is PSC 833.

In another embodiment, the biological response modifiers are selected from the group consisting of monoclonal antibodies and cytokines.

In another embodiment, the cytokines are selected from the group consisting of interferons, interleukins and colony-stimulating factors.

In another embodiment, the biological response modifiers are selected from the group consisting of Rituxan, CMA-676, Interferon-alpha recombinant, Interleukin-2, Interleukin-3, Erythropoetin, Epoetin, G-CSF, GM-CSF, Filgrastim, Sargramostim and Thrombopoietin.

The individual components of such combinations may be administered either sequentially or simultaneously in separate or combined pharmaceutical formulations.

The combinations referred to above may conveniently be presented for use in the form of a pharmaceutical formulation and thus pharmaceutical formulations comprising a combination as defined above together with an acceptable carrier therefor comprise a further aspect of the invention.

In one embodiment of the present invention, the compound of formula (I) present in the pharmaceutical combination of the present invention is (β-L-OddC) and at least one further therapeutic agent is chosen from cytarabine, gemcitabine and idarubicin. Preferably, the ratio of β-L-OddC to the further therapeutic agent is 1:250 to 250:1, more preferably 1:50 to 50:1, especially 1:20 to 20:1.

In one embodiment the present invention provides a method for treating leukemia selected from the group comprising acute myelogenous leukemia (AML), chronic myelogenous leukemia (CML), chronic myelogenous leukemia in blastic phase (CML-BP), refractory myelodysplastic syndromes (MDS).

In one embodiment, the present invention provides a method for treating myelogenous leukemia.

In another embodiment, the present invention provides a novel method for treating acute myelogenous leukemia.

In another embodiment, the present invention provides a novel method for treating chronic myelogenous leukemia.

In another embodiment, the present invention provides a novel method for treating chronic myelogenous leukemia in blastic phase.

Still in another embodiment, the present invention provides a novel method for treating multidrug resistant leukemia.

There is also provided a method for treating leukemia with the pharmaceutically acceptable salts of the compounds of formula I of the present invention. By the term pharmaceutically acceptable salts of the compounds of formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids.

Salts derived from appropriate bases include alkali metal (e.g. sodium), alkaline earth metal (e.g. magnesium), ammonium and $NR_4+$ (where R is $C_{1-4}$ alkyl) salts.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

The term "aryl" represent an unsaturated carbocyclic moiety, optionally mono- or di-substituted with OH, SH, amino, halogen or $C_{1-6}$ alkyl, and optionally substituted by at least one heteroatom (e.g. N, O, or S).

The term "leukemia" represent acute myelogenous leukemia (AML), chronic myelogenous leukemia (CML), chronic myelogenous leukemia in blastic phase (CML-BP), acute lymphocytic leukemia (ALL), chronic lymphocytic leukemia (CLL), hairy cell leukemia (HCL), myelodysplastic syndromes (MDS) and all subtypes of these leukemias which are defined by morphological, histochemical and immunological techniques that are well known by those skilled in the art.

The term "myelogenous leukemia" represent both acute and chronic myelogenous leukemias (AML, CML, CML-BP) which involve the myeloid elements of the bone marrow (e.g. white cells, red cells and megakaryocytes) and includes all subtypes which are defined by morphological, histochemical and immunological techniques that are well known by those skilled in the art.

The term "multidrug resistant leukemia" represent a leukemia which is non responsive to treatment with chemotherapeutic agents.

The term "host" represent any mammals including humans.

In one embodiment, the host is human.

According to one embodiment, the patient that has been previously treated is resistant to STI-571. The patient is treated according to any one of the methods set forth herein.

According to another embodiment, the patient is refractory to STI-571.

The terms "resistant to STI-571" and "refractory to STI-571" represent a patient previously treated with STI-571 which was either non responsive to treatment with STI-571 or had a response to treatment with STI-571 and then relapsed.

Similarly, the term "refractory leukemia" represents previously treated patients which were either non responsive to treatment with the agent or had a response to treatment and then relapsed.

It will be appreciated that the amount of a compound of formula (I) of the present invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.01 to about 750 mg/kg of body weight per day, preferably in the range of 0.5 to 60 mg/kg/day, most preferably in the range of 1 to 20 mg/kg/day. More particularly, chemotherapeutic drugs are given in dosages of mg/m$^2$ of body weight per day. In general a suitable dose will be in the range of from about 0.72 to about 10 mg/m$^2$ per day, preferably in the range of 0.72 to about 8 mg/m$^2$ per day, and most preferably 8 mg/m$^2$ per day. All of the previous doses are usually administered over a 30 minutes intravenous infusion period.

The desired dose may conveniently be presented in a single dose or as divided dose administered at appropriate intervals, for example as two, three, four or more doses per day.

In one embodiment, the compound of formula (I) of the present invention is administered to the patient that has been previously treated with STI-571 and has become resistant to the STI-571 treatment at a dose of 8 mg/m$^2$ over 30 minutes intravenous infusion per day for 5 days.

The pharmaceutical combination according to the present invention is conveniently administered in unit dosage form; for example containing 10 to 1500 mg, conveniently 20 to 1000 mg, most conveniently 50 to 700 mg of active ingredient per unit dosage form.

Ideally, the active ingredient is administered to achieve peak plasma concentrations of the active compound of from about 1 to about 75 $\mu$M, preferably about 2 to 50 $\mu$M, most preferably about 3 to about 30 $\mu$M. Ideally, the peak plasma concentration of the active compound is 5 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient. Also, desirable blood levels may be maintained by a 30 minute infusion to provide about 0.72 to about 10 mg/m$^2$ per day for 5 days.

While it is possible that, for use in therapy, a compound of formula (I) of the present invention may be administered as the raw chemical, it is preferable according to one embodiment of the invention, to present the active ingredient as a pharmaceutical formulation. The embodiment of the invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include but are not limited to those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods according to this embodiment include the step of bringing into association the active compound with liquid carriers or finely divided solid carriers or both and then, if necessary, shaping the product into the desired formulation.

Pharmaceutical formulation suitable for oral administration are conveniently presented as discrete units such as capsules, cachets or tablets each containing a predetermined amount of the active ingredient; as a powder or granules. In another embodiment, the formulation is presented as a solution, a suspension or as an emulsion. Still in another embodiment, the active ingredient is presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula (I) according to the present invention may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

The pharmaceutical combination according to the invention may also be formulated for direct administration to the Central Nervous System by intravenous administration. In addition, administration to the heart may be achieved.

For topical administration to the epidermis, the compounds of formula I, may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid. In another embodiment, they are presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

According to one embodiment, the formulations suitable for vaginal administration are presented as pessaries, tampons, creams, gels, pastes, foams or sprays containing in addition to the active ingredient such carriers as are known in the art to be appropriate.

For intra-nasal administration the compounds of formula (I) may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds of formula (I) may be conveniently delivered from an insufflator, nebulizer or a pressurized pack or other convenient means of delivering an aerosol spray. In another embodiment, pressurized packs comprise a suitable propellant such as dichlorodifluoromethane, trichlorofluoromethane, dichlorotetrafluoroethane, carbon dioxide or other suitable gas. In another embodiment, the dosage unit in the pressurized aerosol is determined by providing a valve to deliver a metered amount.

Alternatively, for administration by inhalation or insufflation, the compounds of formula I according to the present invention are in the form of a dry powder composition, for example a powder mix of the compound and a suitable powder base such as lactose or starch. In another embodiment, the powder composition is presented in unit dosage form in, for example, capsules or cartridges or e.g. gelatin or blister packs from which the powder may be administered with the aid of an inhaler or insufflator.

When desired the above described formulations adapted to give sustained release of the active ingredient may be employed.

The following examples are provided to illustrate various embodiments of the present invention and shall not be considered as limiting in scope.

The compounds of formula (I), including but not limited to β-L OddC, were synthesized at Shire BioChem Inc. as previously described in PCT publication numbers WO96/07413A1, WO97/21706 and WO00/47759.

EXAMPLE 1

A preliminary study was conducted to investigate the activity of β-L Oddc in patients with chronic myeloid leukemia in blastic phase (CML-BP). The multicenter study was conducted using β-L Oddc $8mg/m^2$/day daily for 5 days for patients with CML-BP who had received no prior chemotherapy for CML-BP. Patients who had received Gleevec therapy as sole prior therapy for CML-BP were also eligible. Twenty-six patients, 17 male, 26 performance score less than or equal to 2, median age 54 years (range 31–84) had been entered in the study to date. 13 (50%) patients received β-L Oddc as first therapy for CML-BP, 13 (50%) had failed prior Gleevec therapy for CML-BP. Response definitions are as follows: Complete hematologic response (CHR) requires normalization of peripheral counts and differentials with less than or equal to 5% marrow blasts for at least 4 weeks. Hematologic improvement (HI) is as with CHR but with persistence of thrombocytopenia less than $100 \times 10^9$/L and few immature peripheral cells. A partial hematologic response (PHR) is as per CHR, but allows persistence of, though less than or equal to 50% reduction of, palpable splenomegaly and thrombocytosis (platelets>$450 \times 10^9$/L) or the presence of few immature peripheral cells. Back to second chronic phase (BCP) requires disappearance of BP features and return to chronic phase CML features, ie. peripheral blasts<15%, peripheral blasts+ promyelocytes<30%, peripheral basophils<20% and platelets>$100 \times 10^9$/L. In patients with extramedullary disease (EMD) complete response (CR) requires CHR plus disappearance of all EMD. PR in patients with EMD require at least a 50% reduction in all EMD.

In preliminary results, twenty one patients who had received a total of 40 cycles (range 1 to 4) of β-L Oddc therapy were valuable for response and some responses were observed in 4 patients. The study was not completed and the data was not verified for complete analysis.

EXAMPLE 2

Evaluation of β-L Oddc in vitro Study

β-L Oddc was evaluated using an in vitro growth inhibition (MTS) assay. The description of the cell lines used and the details of the MTS assay are described below.

Cell lines: Two human CML, Ph+, p210 Bcr-Abl expressing cell lines were used, namely, KBM-5 and KBM-7. KBM-5 was derived from a patient in the blastic phase of CML and was evaluated to be absent of normal c-ABL. KBM-7 was identified previously to be a human near-haploid cell line. These two cell lines were further described in the references below, now incorporated by reference:

1. Beran M., Pisa p., O'Brien S., Kurzrock R., Siciliano M., Cork A., Andersson B S., Kohli V., Kantarjian H., Biological Properties and growth in SCID mice of a new myelogenous leukemia cell line (KBM-5) derived from chronic myelogenous leukemia cells in the blastic phase. Cancer Research, 53(15): 3603–3610, 1993.
2. Kotecki M., Reddy P S., Cochran B H., Isolation and characterization of a near-haploid human cell line, Exp. Cell. Res., 252(2): 273–280, 1999
3. Andersson B S., Collins V P., Kurzrock R., Larkin D W., Childs C., Ost A., Cork A., Trujillo J M., Freireich E J., Siciliano M J., Leukemia, 9(12): 2100–2108, 1995.

The KBM-5 and KBM-7 cell differ in their inherent sensitivity to STI-571 and in their response to STI-571 exposure. The cells were cultured in Iscove's modified Dulbecco's medium supplemented with 10% fetal calf serum (Invitrogen Corp., Carlsbad, Calif.) at 37° C. in atmosphere of 5% $CO_2$ in air. These cells also differ in their response to STI-571 exposure: G0/G1 cell cycle arrest in KBM5 vs. apoptosis in KBM7.

Generation of STI-571-resistant KBM5 and KBM7 Ph+ cell lines: STI571 resistant cell lines were developed by culturing the cells with increasing concentrations of STI-571, as described in detail below. Cells maintained in liquid cultures were exposed to increasing concentrations of STI-571, starting with a concentration of 0.05 μM, and increasing gradually at a rate of 0.1 μM. When the survival of the cells grown in a given STI-571 concentration reached 80%, a proportion of cells were frozen while the remaining cells were grown at a next higher drug level. In this way, subpopulations of cells with different degree of resistance were generated (e.g, KBM5-STIR$^{0.75}$ indicating KMB5 cells resistant to STI-571 at the dose of 0.075 μM). The resistance was defined as the ability of cells to survive (at least 80% survival) and proliferate indefinitely in continuous presence of a given concentration of STI-571. The resistant cells emerged earlier in KBM5 than in KBM7 cells and this reflected the lower inherent sensitivity of these cells, as recently reported. Thus, KBM5 cells were able to survive in 1.0 μM of STI-571 4 months after the initiation of the experiments, whereas a similar level or resistance was reached only after 10 months in KBM7 cells. KBM5-STI$^{R1.0}$ and KBM7-STI$^{R1.0}$, the sublines with the highest level of resistance, showed an $IC_{50}$ about twenty times higher than the value calculated in the corresponding cell line.

Growth inhibition (MTS) assay: The in vitro growth inhibition effect of β-L Oddc on leukemic cells was determined by measuring MTS (CellTiter 96®Aqueous One Solution Reagent, Promega Corporation, WI) dye absorbance by living cells. Briefly, cells were seeded in triplicate in 96-well microtiter plates (Falcon, USA) at a concentration of 4×10$^5$ cells /ml. After exposure to the β-L Oddc for 72 h, 20 μl of MTS solution were added to each well, the plates were incubated for additional 4 h at 37° C., and absorbance at 490 nm was measured.

Figure 1:
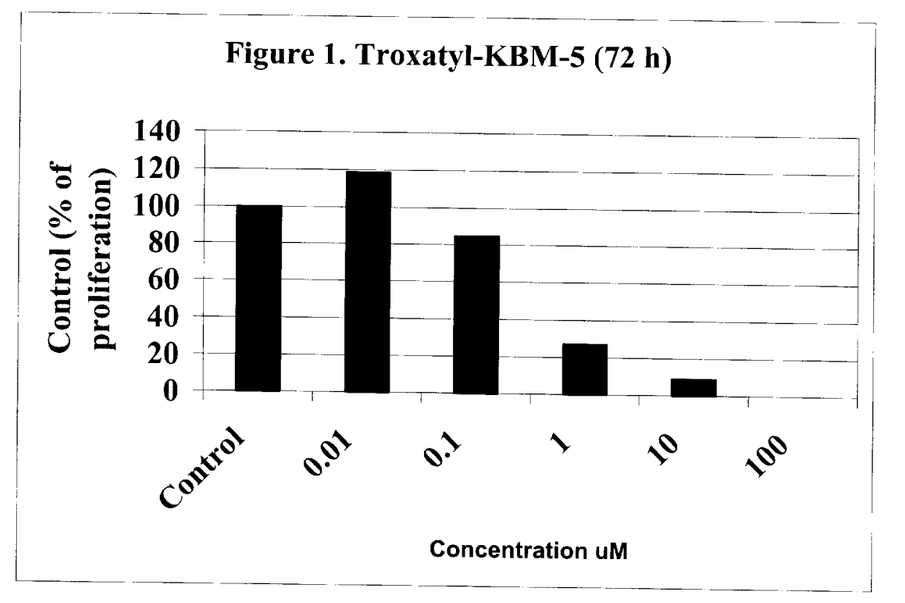
FIGS. 1–4 demonstrate the results obtained for a growth inhibition assay in which the in vitro growth inhibition effect of B-L-Oddc on leukemic cells was determined by measuring MTS dye absorbance on living cells from four separate lines: KBM-5 (FIG. 1), KBM-5R (FIG. 2), KBM-7 (FIG. 3), and KBM-7R (FIG. 4).
Figure 2:
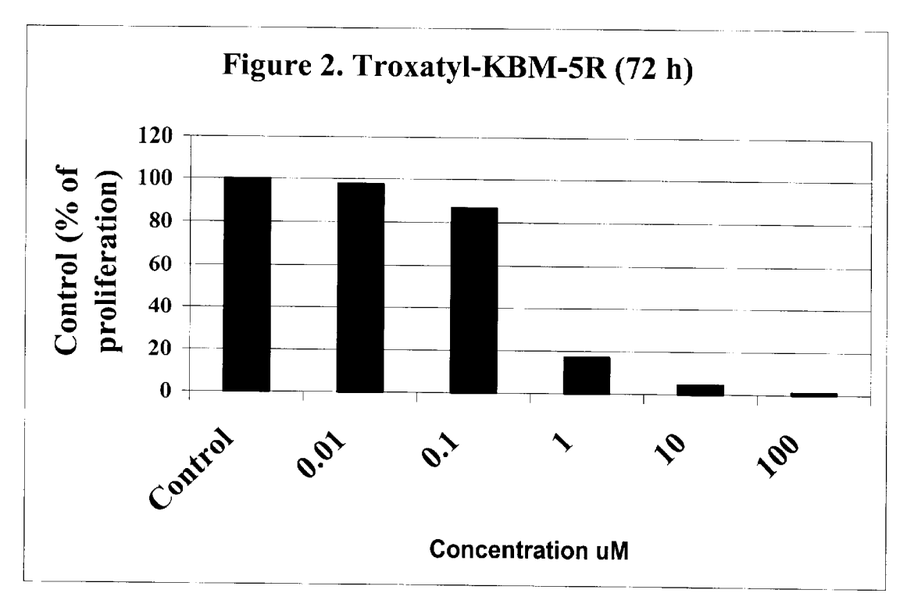
Figure 3:
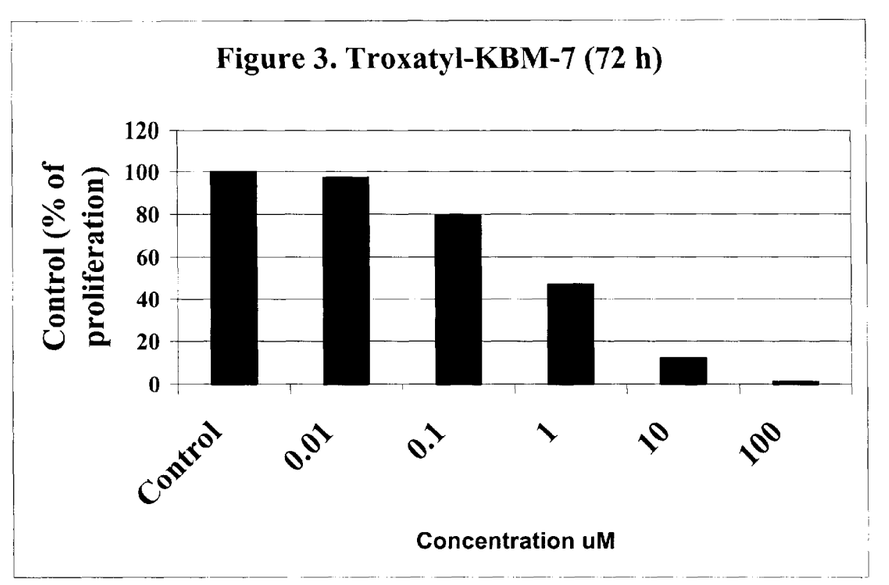
Figure 4:
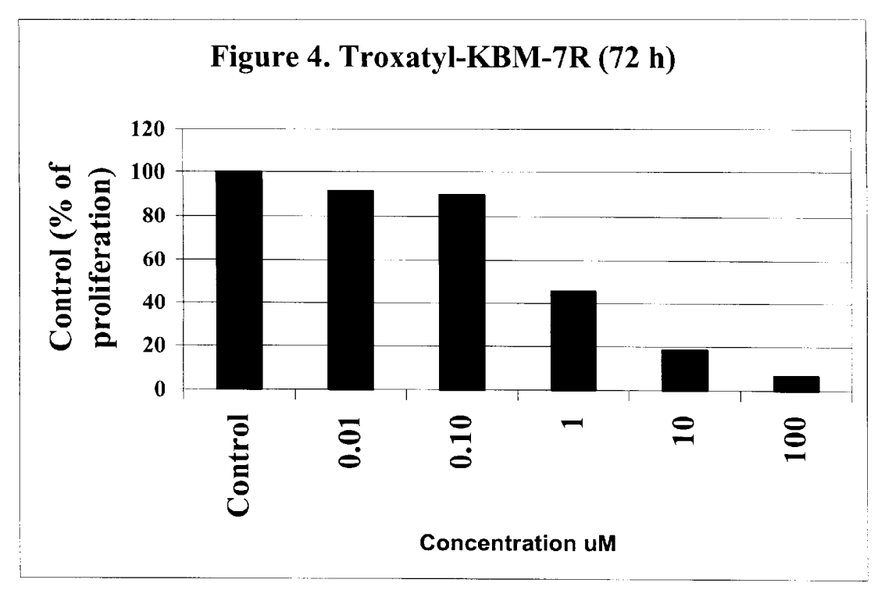

The results, as shown in FIGS. 1–4, indicated that in the 3 day MTS assay, in all 4 cell lines (KBM-5, KBM-7, KBM5-STI$^R$ and KBM7-STI$^R$) the $IC_{50}$ value was between 0.5 to 1.0 μM. The $IC_{50}$ value is defined to be the drug concentration which causes 50% growth inhibition. Therefore, it can be concluded from these results that β-L Oddc was equally sensitive in KBM-5 and KBM-7 cells and the STI-571-resistant KBM5 and KBM7 cell lines.

We claim:

1. A method for treating a patient with leukemia comprising administering to a patient that has been previously treated with a Bcr-Abl tyrosine kinase inhibitor a therapeutically effective amount of a compound having the formula I:

(I)

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and wherein each Rc is independently selected from H, $C_{1-6}$ alkyl, $C_{2-6}$ alkenyl, $C_{2-6}$ alkynyl and an hydroxy protecting group.

2. A method for treating a patient with leukemia comprising administering to a patient that has been previously treated with imatinib mesylate (STI-571) and has become resistant to the imatinib mesylate (STI-571) treatment, a therapeutically effective amount of a compound having the formula I:

(I)

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and wherein each Rc is independently selected from H, $C_{1-6}$ alkyl, $C_{2-6}$ alkenyl, $C_{2-6}$ alkynyl and an hydroxy protecting group.

3. The method according to claim 1, wherein R is H.

4. The method according to claim 1, wherein B is cytosine.

5. The method according to claim 1, wherein R is H and B is cytosine.

6. The method according to claim 1, wherein said compound of formula I is at least 95% free of the (+) form.

7. The method according to claim 1, wherein said compound of formula I is at least 97% free of the (+) form.

8. The method according to claim 1, wherein said compound of formula I is at least 99% free of the (+) form.

9. The method according to claim 1, wherein said compound of formula I is substantially in the form of the (−) enantiomer.

10. The method according to claim 1, wherein said compound of formula I is β-L Oddc.

11. The method of claim 1, wherein the leukemia is a chronic myelogenous leukemia.

12. The method of claim 1, wherein the leukemia is an acute myelogenous leukemia.

13. The method of claim 1, wherein the leukemia is a chronic myelogenous leukemia in blastic phase.

14. The method according to claim 2, wherein R is H.

15. The method according to claim 2, wherein B is cytosine.

16. The method according to claim 2, wherein R is H and B is cytosine.

17. The method according to claim 2, wherein said compound of formula I is at least 95% free of the (+) form.

18. The method according to claim 2, wherein said compound of formula I is at least 97% free of the (+) form.

19. The method according to claim 2, wherein said compound of formula I is at least 99% free of the (+) form.

20. The method according to claim 2, wherein said compound of formula I is substantially in the form of the (−) enantiomer.

21. The method according to claim 2, wherein said compound of formula I is $\mu$-L Oddc.

22. The method of claim 2, wherein the leukemia is a chronic myelogenous leukemia.

23. The method of claim 2, wherein the leukemia is an acute myelogenous leukemia.

24. The method of claim 2, wherein the leukemia is a chronic myelogenous leukemia in blastic phase.

25. A method for treating leukemia in a patient comprising administering to a patient that has been previously treated with a Bcr-Abl tyrosine kinase inhibitor a therapeutically effective amount of at least one compound of general formula I wherein B is cytosine or 5-fluorocytosine and R is selected from H, monophosphate, diphosphate, triphosphate, carbonyl substituted with a $C_{1-4}$ alkyl, $C_{2-6}$ alkenyl, $C_{2-6}$ alkynyl, $C_{6-10}$ aryl, and wherein each Rc is independently selected from H, $C_{1-6}$ alkyl, $C_{2-6}$ alkenyl, $C_{2-6}$ alkynyl and an hydroxy protecting group, and at least one further therapeutic agent selected from nucleoside analogues, chemotherpeutic agents, multi-drug resistance reversing agents and biological response modifiers.

26. The method according to claim 25, wherein the leukemia is chronic myelogenous leukemia or acute myelogenous leukemia.

27. The method according to claim 25, wherein the leukemia is acute myelogenous leukemia.

28. The method according to claim 25, wherein the leukemia is chronic myelogenous leukemia in blastic phase.

29. The method according to claim 25, wherein the compound of formula I and the further therapeutic agent are administered sequentially.

30. The method according to claim 25, wherein the compound of formula I and the therapeutic agent are administered simultaneously.

31. The method according to claim 2, wherein the compound of formula (I) is administered to the patient that has been previously treated with imatinib mesylate (STI-571) and has become resistant to the imatinib mesylate (STI-571) treatment at a dose of 8 mg/m² over 30 minutes intravenous infusion per day for 5 days.

* * * * *